United States Patent [19]

Dohr et al.

[11] Patent Number: 4,708,973

[45] Date of Patent: Nov. 24, 1987

[54] THERMOPLASTIC POLYAMIDE AS FRAGRANCE CARRIER

[75] Inventors: Manfred Dohr, Duesseldorf-Holthausen; Norbert Wiemers, Monheim; Werner Gruber, Korschenbroich, all of Fed. Rep. of Germany

[73] Assignee: Henkel Kommanditgesellschaft auf Aktien, Duesseldorf, Fed. Rep. of Germany

[21] Appl. No.: 870,651

[22] Filed: May 30, 1986

Related U.S. Application Data

[63] Continuation of Ser. No. 678,329, Dec. 5, 1984, abandoned.

[30] Foreign Application Priority Data

Dec. 19, 1983 [DE] Fed. Rep. of Germany ....... 3345847

[51] Int. Cl.$^4$ .............................................. C08L 77/06
[52] U.S. Cl. ....................................... 523/102; 512/4; 528/336; 528/339.3; 528/340
[58] Field of Search ...................... 523/102; 528/339.3, 528/340, 336; 252/522 A

[56] References Cited

U.S. PATENT DOCUMENTS

| | | |
|---|---|---|
| 3,681,248 | 8/1972 | Gould et al. ............................ 252/89 |
| 3,775,227 | 11/1973 | Wilbert et al. ......................... 161/30 |
| 3,926,655 | 12/1975 | Miles ................................ 252/522 A |
| 3,939,099 | 2/1976 | Tusa et al. ............................ 252/522 |
| 4,051,159 | 9/1977 | Tsoucalas et al. ................... 523/102 |
| 4,218,351 | 8/1980 | Rasmussen ......................... 260/18 N |
| 4,449,987 | 5/1984 | Lindauer .......................... 252/522 A |

FOREIGN PATENT DOCUMENTS

| | | | |
|---|---|---|---|
| 844014 | 6/1970 | Canada ..................................... 400/1 |
| 1319807 | 5/1973 | United Kingdom . | |

*Primary Examiner*—Harold D. Anderson
*Attorney, Agent, or Firm*—Ernest G. Szoke; Henry E. Millson, Jr.; Mark A. Greenfield

[57] ABSTRACT

The use of known thermoplastic polyamides based on dimerized fatty acids and predominantly aliphatic diamines, especially polyether diamines, as carriers for fragrances and perfumes.

17 Claims, No Drawings

THERMOPLASTIC POLYAMIDE AS FRAGRANCE CARRIER

This application is a continuation, of application Ser. No. 678,329, filed Dec. 5, 1984, now abandoned.

BACKGROUND OF THE INVENTION

1. Field of the Invention

This invention relates to the use of specified thermoplastic polyamides as fragrance or perfume carriers.

2. Description of Related Art

It is known that both water-soluble and water-alcohol-soluble plastics can be used as carriers for perfumes. Among the water-soluble plastics, hydrophilic water-soluble polyacrylic acid esters and also quaternized polyvinyl pyrrolidone are particularly effective (see U.S. Pat. Nos. 3,681,248 and 3,939,099).

Among the water-insoluble plastics, polyethylene and polypropylene are particularly effective. In some cases, combinations of polyolefins, such as in particular high-density and low-density polyethylene, are also used (see U.S. Pat. Nos. 3,567,119 and 3,775,227 and Canadian Pat. No. 844,014). Another plastic frequently used for this purpose is PVC or polyurethane foam (see French Pat. No. 1,602,575). Polyvinyl acetate or thermoplastic polyesters or polyamides based on dicarboxylic acids and diamines have also been used as fragrance or perfume carriers.

However, the above-mentioned polymeric compounds, which can optionally be used in conjunction with plasticizers, resins or fillers, are unsatisfactory in certain respects, for example, with respect to the sustained release of the fragrance.

DESCRIPTION OF THE INVENTION

An object of the present invention is to provide carriers for fragrances or perfumes which, on the one hand, have a high retention capacity for those compounds, but which on the other hand also release the active compound fairly uniformly into the surrounding atmosphere. Although it was known that, in many cases, standard commercially available, thermoplastic polyamides show favorable release behavior, the polyamides hitherto recommended for this purpose are still not satisfactory with respect to the uniformity of release of the fragrance into the surrounding atmosphere.

It has now been found that polyamides produced from dimerized fatty acids and diamines show considerably more favorable release behavior than the known polycondensates of dicarboxylic acids and diamines.

Accordingly, the present invention relates to the use of thermoplastic polyamides based on dimerized fatty acids and predominantly aliphatic diamines as carriers for fragrances and perfumes. More particularly, the invention relates to the use of thermoplastic polyamides containing polyether diamines as the main component of the aliphatic diamines.

The above thermoplastic polyamides used in the practice of the invention have been known for some considerable time. For example, suitable polyamides can be produced from so-called dimeric fatty acids, which are obtained by the "polymerization" of unsaturated fatty acids, and one or more of aliphatic diamines, cycloaliphatic diamines, aromatic diamines, heterocyclic diamines, and arylaliphatic diamines. Examples of such diamines include ethylene diamine, hexamethylene diamine, piperazine, diaminodiphenylmethane, and oligomeric amino-terminated polyethers (see, for example, U.S. Pat. No. 4,218,351 which is incorporated herein by reference). In this connection, the percentage of short-chain diamines should amount to more than about 60 mole percent while the percentage containing the skeleton of the dimerized fatty acids should amount to less than about 40 mole percent. In addition, thermoplastic polyamides of similar structure are known from British Pat. No. 1,319,807, differing only slightly with respect to the amine component which contains ether groups. It has now been discovered that such polyamides derived from diamines containing polyether groups (polyether diamines) are superior in terms of their fragrance and perfume release behavior to polyamides of the type derived from short-chain aliphatic diamines (particularly ethylene diamine). In one particularly preferred embodiment, the invention relates to the use as carriers for fragrances and perfumes of thermoplastic polyamides which have been obtained by the condensation of (a) from about 40 to about 48 mole percent of dimeric fatty acids,
(b) from about 2 to about 10 mole percent of monomeric fatty acids,
(c) from about 4 to about 25 mole percent of polyether diamines having a molecular weight of from about 500 to about 5000, and
(d) from about 25 to about 46 mole percent of aliphatic diamines.

Among the polyether diamines used as building blocks for the polyamides, those corresponding to the following general formula

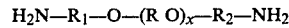

$$H_2N-R_1-O-(R\ O)_x-R_2-NH_2$$

are particularly suitable. In this formula, x is a number of from 8 to 80 and preferably from 8 to 40, $R_1$ and $R_2$ can be the same or different and represent $C_2-C_6$ aliphatic and/or cycloaliphatic hydrocarbon radicals and R is an optionally branched aliphatic hydrocarbon radical containing from 1 to 6 carbon atoms or the RO group can be a tetrahydrofuran group.

The dimerized fatty acids used in the production of the polyamides are frequently referred to as polymeric fatty acids and are obtained by the polymerization of olefinically unsaturated $C_{12}-C_{22}$ fatty acids. They also include mixtures of different polymeric fatty acids which have a predominant content, i.e. more than 70%, of dimeric fatty acid and which additionally contain a small percentage of monocarboxylic acids. These monocarboxylic acids also contain from 12 to 22 carbon atoms, and can contain double bonds and branches.

As discussed above, the polyether diamines used in forming the polyamides are also known compounds. Typical representatives of the polyether diamines are bis-(2-aminopropyl)-polyoxypropylenes and bis-(3-amino-propyl)polytetrahydrofurans, which have a molecular weight of from about 500 to about 5000. They are preferred by virtue of their ready availability. Polyethers containing two terminal amino groups synthesized from polymeric, optionally branched-chain butane diols, pentane diols and hexane diols are also suitable.

Finally, in addition to the polyether diamines, diamines with a linear or branched chain containing more than two carbon atoms, such as ethylene diamine, 1,3-diaminopropane, 1,4-diaminobutane, neopentyl diamine, hexamethylene diamine and trimethyl hexamethylene diamine can be used in the production of the polyamides. Diamines obtained from dimerized fatty acids with the carboxyl groups substituted by amino groups can also be used. Compounds of this type are frequently referred to as dimeric diamines. Cycloaliphatic diamines, arylaliphatic diamines, or aryldiamines, such as diaminodicyclohexyl methane; 3-amino-methyl-3,5,5-trimethyl · cyclohexylamine; diaminodiphenylmethane; xylylene diamine; piperazine; dimethylaminopiperazine; and dipiperidyl propane can also be used as the diamines.

In addition to the dimerized fatty acids, there can also be added to the polymerization mixture small quantities of aliphatic dicarboxylic acids, primarily adipic acid, azeleic acid, sebacic acid, and decane dicarboxylic acid.

The polyamides used in accordance with the invention are obtained by melt condensation using known processes. The acid components react with the amino components at temperatures of from about 150 to about 250° C., the water of reaction being removed by distillation or, if necessary, using an azeotropic solvent and/or a vacuum. By carrying out the reaction using a small excess of acid or amine function, the amine or acid number may be influenced in known manner. The amine number should have values of from about 0.3 to about 10, and preferably of from about 0.5 to about 6 while the acid number should be between about 0.5 and about 15, and preferably between about 1.0 and about 10. The softening point should be above 80° C. and should not exceed 150° C.

The polyamides used in accordance with the invention are distinguished not only by a favorable softening point, they also show a favorable processing viscosity, i.e. they suddenly assume a very low viscosity beyond the softening range. In general, they are characterized by good film-forming properties and show a smooth surface. Their adhesion to most substrates is very good so that they anchor themselves to a variety of different substrates without any need for special pretreatment. Their resistance to chemicals is also very good, i.e. they are resistant in particular to alkalis and acids.

The known fragrances and perfumes can readily be incorporated in the above polyamides in a concentration of from about 1 to about 30% by weight, based on the weight of polyamide. It should be noted that the invention does not reside in the choice of a particular fragrance or perfume. In some cases, it is advantageous to use relatively small quantities, i.e. up to about 25%, based on the polyamide, of known plasticizers such as, for example, epoxidized fatty acid esters, which also function as stabilizers, or phosphoric acid esters, or sulfonic acid esters of phenols. It is also possible, if desired, to use pigments or fillers, such as, for example, chalk or barium sulfate, or silica-containing fillers, such as precipitated silica or calcium silicate, solium aluminum silicate, or Neuenburger Kreide. Pigments, such as iron oxide or phthalocyanides, can also be used for coloring.

By virtue of the affinity of most fragrances and perfumes for the polyamides, losses during processing of the mixtures of polyamides, fragrances and perfumes and, optionally, other auxiliaries are minimal. As a result, the extent to which the people concerned with processing are affected by fumes is minimal compared with corresponding work involving other polymer-based carriers.

The release behavior of the mixtures of polyamides and fragrances or perfumes was assessed by the gravimetric method and by a subjective method involving experts. In the gravimetric method, the samples are observed over a relatively long period, optionally under thermal load, and the relative reduction in weight determined. This method is particuarly suitable when relatively large quantities of fragrances or perfumes have been incorporated in the polyamide. It is particularly in the case of strong-smelling perfumes that the reduction in the strength of the fragrance is assessed by experts. This method also provides good, reproducible results and confirms the superiority of the polyamides used in accordance with the invention as carriers.

According to the invention, the thermoplastic polyamides containing a fixed fragrance or perfume can be used for the following applications:

Perfuming of solid detergents and cleaners: by applying a fragrance-containing film to the upper container wall or beneath the lid of detergent and cleaner packs. By virtue of their favorable adhesive properties, the thermoplastic polyamides adhere firmly to a variety of different packaging materials (absorbent and nonabsorbent surfaces).

Odor masking in automatic dishwashing machines: by applying a fragrance-containing film to the inner wall of a dishwashing machine. Since the fragrance-carrying polyamides are resistant to the alkaline conditions in the dishwashing machine, they last for numerous washing cycles.

Freshening of washing in tumbler washing machines: by introducing a fragrance-impregnated nonwoven polyamide or by coating a tape or foam strip backed by a layer of pressure-sensitive adhesive.

Internal coating of film supports: fragrance-impregnated polyamide is applied to the inner support of a roll of paper or film.

Application to domestic appliances: after installation, the molten polyamide or an adhesive-coated polyamide strip is applied for subsequent odor improvement.

Fragrance release in vacuum cleaners: fragrance-impregnated granulate is introduced into the air stream (bag) of vacuum cleaners so that, when the cleaner is in use, a fragrance note is added to the issuing air stream over a prolonged period.

Odor masking in dry cleaning installations: after cleaning with halogenated hydrocarbons, drying may be carried out in the presence of the fragrance-carrying thermoplastic polyamides. The polyamides are particularly resistant to dry cleaning chemicals.

The invention will be illustrated but not limited by the following examples.

EXAMPLES

A polyamide suitable for the purposes of the invention was produced by condensing 759 g of dimerized $C_{18}$ fatty acid (72% of dimeric fractions)
60 g of tall oil fatty acid
81 g of ethylene diamine and
112 g of bis-(3-aminopropyl)-polytetrahydrofuran (molecular weight 750).

Condensation was commenced under nitrogen at 60° C., the temperature being increased over a period of 1 hour to 230° C. and kept at that level for 1 hour. The reaction vessel was evacuated to 15 mbar and volatile fractions removed.

The polyamide had an acid number of 9.8, an amine number of 0.7 and a softening point of +105° C.

By heating 80% of the polyamide with 5% of adipic acid dioctyl ester and 15% of perfume oil, a mixture was prepared and subsequently cast into 5 mm thick panels. Testing of the fragrance-carrying polyamides for their fragrance release capacity:

Test panels were stored at 50° C. in a recirculating air drying cabinet and the weight loss based on the fragrance used was measured. A flowery fresh-smelling oil was used as the perfume oil. The weight loss during storage in the recirculating air drying cabinet, based on the perfume oil used, amounted to 15% after 1 day
25% after 3 days
55% after 7 days
85% after 14 days Storage in the open in a room kept at 25° C. produced the following results:

8% after 1 day
25% after 1 week
50% after 5 weeks
65% after 10 weeks

What is claimed is:

1. A thermoplastic polyamide and fragrance or perfume composition consisting essentially of:
   (A) a thermoplastic polyamide which is the condensation reaction product of:
   (1) at least one dimeric fatty acid present in about 40 to about 48 mol percent;
   (2) at least one monomeric fatty acid present in about 2 to about 10 mol percent;
   (3) at least one polyether diamine having a molecular weight of about 500 to about 5,000 present in about 4 to about 25 mol percent; and
   (4) at least one aliphatic diamine present in about 25 to about 46 mol percent; and
   (B) a fragrance or perfume incorporated within said thermoplastic polyamide in a concentration of about 1 to about 30 percent by weight, based upon the weight of said polyamide.

2. The composition of claim 1 wherein said polyether diamine component (A) (3) has the formula:

$$H_2N-R_1-O-(RO)_x-R_2-NH_2$$

wherein:
x is an integer of from 8 to 80,
$R_1$ and $R_2$ are the same or different and are each a divalent $C_{2-6}$-aliphatic hydrocarbon or cycloaliphatic hydrocarbon radical, and
R is a branched or unbranched $C_{1-6}$-aliphatic hydrocarbon or RO is a divalent poly (tetrahydrofuran) radical.

3. The composition of claim 1 wherein said dimeric fatty acid component (A) (1) and said monomeric fatty acid component (A) (2) are each a $C_{12-22}$ fatty acid, each containing double bonds or not containing double bonds, each containing branched chains or not containing branched chains.

4. The composition of claim 2 wherein said dimeric fatty acid component (A) (1) and said monomeric fatty acid component (A) (2) are each a $C_{12-22}$ fatty acid, each containing double bonds or not containing double bonds, each containing branched chains or not containing branched chains.

5. The composition of claim 3 wherein x is an integer of from 8 to 40.

6. The composition of claim 4 wherein x is an integer of from 8 to 40.

7. The composition of claim 1 wherein said thermoplastic polyamide (A) further includes as a reaction component thereof:
   (5) at least one aliphatic dicarboxylic acid consisting essentially of adipic acid, azeleic acid, sebacic acid, or decane dicarboxylic acid.

8. The composition of claim 1 further containing:
   (C) at least one plasticizer which is an epoxidized fatty acid ester, a phosphoric acid ester, or a sulfonic acid ester of a phenol, present in up to 25 percent by weight, based upon the weight of said polyamide.

9. The composition of claim 1 wherein:
   (A)(1) is a dimerized $C_{18}$ fatty acid containing 72 percent of dimeric fractions;
   (2) is a tall oil fatty acid;
   (3) is ethylene diamine;
   (4) is bis-(3-aminopropyl)-polytetrahydrofuran.

10. The composition of claim 8 wherein:
    (A) is present in about 80 percent by weight;
    (1) is a dimerized C18 fatty acid containing 72 percent of dimeric fractions;
    (2) is a tall oil fatty acid;
    (3) is ethylene diamine;
    (4) is bis-(3-aminopropyl)-polytetrahydrofuran;
    (B) is present in about 15 percent by weight; and
    (C) is an adipic acid dioctyl ester and is present in about 5 percent by weight.

11. The composition of claim 1 wherein said polyamide has an amine number of about 0.3 to about 10.

12. The composition of claim 1 wherein said polyamide has an amine number of about 0.5 to about 6.

13. The composition of claim 1 wherein said polyamide has an acid number of about 0.5 to about 15.

14. The composition of claim 11 wherein said polyamide has an acid number of about 0.5 to about 15.

15. The composition of claim 1 wherein said polyamide has an acid number of about 1 to about 10.

16. The composition of claim 12 wherein said polyamide has an acid number of about 1 to about 10.

17. The composition of claim 1 wherein said polyamide has a softening point above 80° C. but not exceeding 150° C.

* * * * *